United States Patent [19]

Karwat

[11] 4,436,707

[45] Mar. 13, 1984

[54] METHOD FOR THE REMOVAL OF ACIDIC GASES SUCH AS CARBON DIOXIDE FROM GASEOUS MIXTURES

[75] Inventor: Heinz Karwat, Pullach, Fed. Rep. of Germany

[73] Assignee: Linde Aktiengesellschaft, Fed. Rep. of Germany

[21] Appl. No.: 510,155

[22] Filed: Jun. 30, 1983

Related U.S. Application Data

[63] Continuation of Ser. No. 322,417, Nov. 18, 1981, abandoned.

[30] Foreign Application Priority Data

Nov. 20, 1980 [DE] Fed. Rep. of Germany ....... 3043831

[51] Int. Cl.³ .............................................. B01D 53/34
[52] U.S. Cl. .................................... 423/226; 423/234; 55/68; 55/73
[58] Field of Search ....................... 423/220, 226, 234; 55/68, 73

[56] References Cited

U.S. PATENT DOCUMENTS 4,250,150 2/1981 Karwat et al. ...................... 423/226

FOREIGN PATENT DOCUMENTS 2759123 7/1979 Fed. Rep. of Germany .......... 55/68

*Primary Examiner*—Earl C. Thomas
*Attorney, Agent, or Firm*—Lerner, David, Littenberg, Krumholz & Mentlik

[57] ABSTRACT

Methods for removing acidic gases from gaseous mixtures, such as hydrocarbon containing gaseous mixtures, are disclosed. The method includes washing the gaseous mixtures with a methanol wash stream containing more than about 0.5 weight percent ammonia therein, so as to remove at least a portion of the acidic gases from the gaseous mixtures and to produce a laden methanol stream containing said acidic gases therein, regenerating said laden methanol stream by removing a portion of said acidic gases therefrom, so as to regenerate said wash stream, and recycling the regenerated wash stream.

6 Claims, 2 Drawing Figures

METHOD FOR THE REMOVAL OF ACIDIC GASES SUCH AS CARBON DIOXIDE FROM GASEOUS MIXTURES

This is a continuation, of application Ser. No. 322,417 filed Nov. 18, 1981, and now abandoned.

FIELD OF THE INVENTION

The present invention relates to methods for the removal of acidic gases, such as carbon dioxide, from gaseous mixtures. More particularly, the present invention relates to such methods for removal of acidic gases by washing with a wash liquid which consists primarily of methanol, and which is regenerated thereafter.

BACKGROUND OF THE INVENTION

Methods for the removal of acidic gases from gaseous mixtures employing methanol as the wash liquid are known, such as is shown in DE-OS 27 59 123. The method described in this patent application uses washing liquids such as methanol for the separation of acidic gases from gaseous mixtures. This washing is primarily accomplished with ammonia, which can increase the effectiveness thereof. However, with respect to the upper limits for the use of such additional ammonia therein, it is required that the ammonia concentration be not more than 0.5 weight percent in the washing liquid. This stringent requirement is said to be based upon the fact that at higher ammonia concentrations, the solid precipitate of ammonium compounds is observed. Therefore, based upon these relatively low permissible ammonia concentrations, it is possible by employing a cleaning column of relatively narrow dimensions to obtain a satisfactory cleaning with minute concentrations of acidic gases remaining in the washed gas. A noticeable decrease in the demands for washing liquid and a reduction of the amount of hydrocarbons unintentionally solved during the treatment of gases containing the same cannot be achieved with these small ammonia additions.

It is therefore an object of the present invention to provide a method of this type which, however, achieves improved efficiencies of operation thereover. In particular, this is desired with respect to the undesired co-absorption of hydrocarbons.

SUMMARY OF THE INVENTION

In accordance with the present invention, these and other objects have now been achieved by the unexpected discovery that such a method can be achieved by direct contradiction of the teachings of the prior art, namely, by using a process in which the regenerated washing liquid contains ammonia concentrations of greater than about 0.5 weight percent. In particular, the present invention includes a method for removing acidic gases from gaseous mixtures by washing the gaseous mixtures with a wash methanol stream comprising greater than about 0.5 weight percent of ammonia therein, so as to remove at least a portion of the acidic gases from the gaseous mixture and to produce a laden methanol stream containing the acidic gases therein, regenerating the laden methanol stream by removing a portion of those acidic gases therefrom so as to regenerate the wash stream therefrom, and recycling the regenerated wash stream. The regenerated methanol stream can thus now be reused for further acidic gas removal.

In accordance with one embodiment of the method of the present invention, the acidic gases generally comprise $CO_2$, although other such gases such as $H_2S$ can also be removed thereby.

In accordance with the preferred embodiment of the method of the present invention, the mole ratio of the ammonia to the acidic gases in the laden methanol stream is less than about 2:1, and preferably less than about 1:1. In particular, the acidic gases in the methanol in accordance with this process are chemically bonded to the ammonia contained therein.

In accordance with the other embodiments of the method of the present invention, the wash stream includes water, preferably in amounts of about 1–20 weight percent.

In accordance with a preferred embodiment of the method of the present invention, the gaseous mixture is a hydrocarbon-containing gaseous mixture, such as natural gas.

In accordance with this invention, relatively higher ammonia concentrations than those which have previously been utilized are now deemed permissible and, in fact, constitute the core of this invention. Thus, contrary to the present concerns of those experts in this art, the solid precipitates of ammonia compounds are eliminated in spite of the use of these increased ammonia concentrations therein. Due to the presence of a salt-type bond from $CO_2$ and $NH_3$ in the laden washing liquid containing acidic gases in the bottom of the washing column, the solubility of hydrocarbons is considerably lower therein, without however influencing the ability for absorption of the disadvantageous $CO_2$ acidic gas therein.

The molar relationship between $NH_3$ and $CO_2$ in the laden methanol stream which is to be regenerated is 2 or less, and preferably less than 1, while the molar relationship between $NH_3$ and $CO_2$ in the regenerated washing liquid or methanol is approximately 2 or less. Thus, this regenerated liquid contains $CO_2$ in a chemical bond with the ammonia, and this turns out to be an advantage in accordance with this invention. Additionally, the washing liquid contains water, advantageously in amounts of about 1 to 20 weight percent therein.

The method of this invention can therefore be utilized in connection with all gaseous mixtures from which acidic gases are to be removed, particularly the acidic gas carbon dioxide. The particular method illustrated herein, however, concerns synthesized gases for the production of ammonia or methanol obtained from the partial oxidation of carbon-containing fluids. Distinct advantageous results are obtained when the method of this invention is applied to gaseous mixtures containing hydrocarbons whose simultaneous cleaning during the separation of the acidic gases is not intended. It has thus been observed that when treating such gaseous mixtures, considerable amounts of hydrocarbons contained in the methanol are generally absorbed therein, and this separation generally requires additional expenditures thereafter. By applying the present method, however, on such gaseous mixtures containing such hydrocarbons, the portion of such hydrocarbons which are carried along during the washing process can be considerably decreased in that liquid. In particular, in accordance with applicant's test results, this decrease in the loss of hydrocarbons in the cleaning column appears to be in the magnitude of about 50%.

The present invention can therefore be applied with special advantage for the cleaning of natural gas always containing, in addition to the methane contained therein, certain amounts of higher hydrocarbons which are highly soluble in pure methanol.

BRIEF DESCRIPTION OF THE DRAWINGS

The present invention may be more fully understood with reference to the following detailed description, and to the figures, in which.

DETAILED DESCRIPTION

Figure 1:
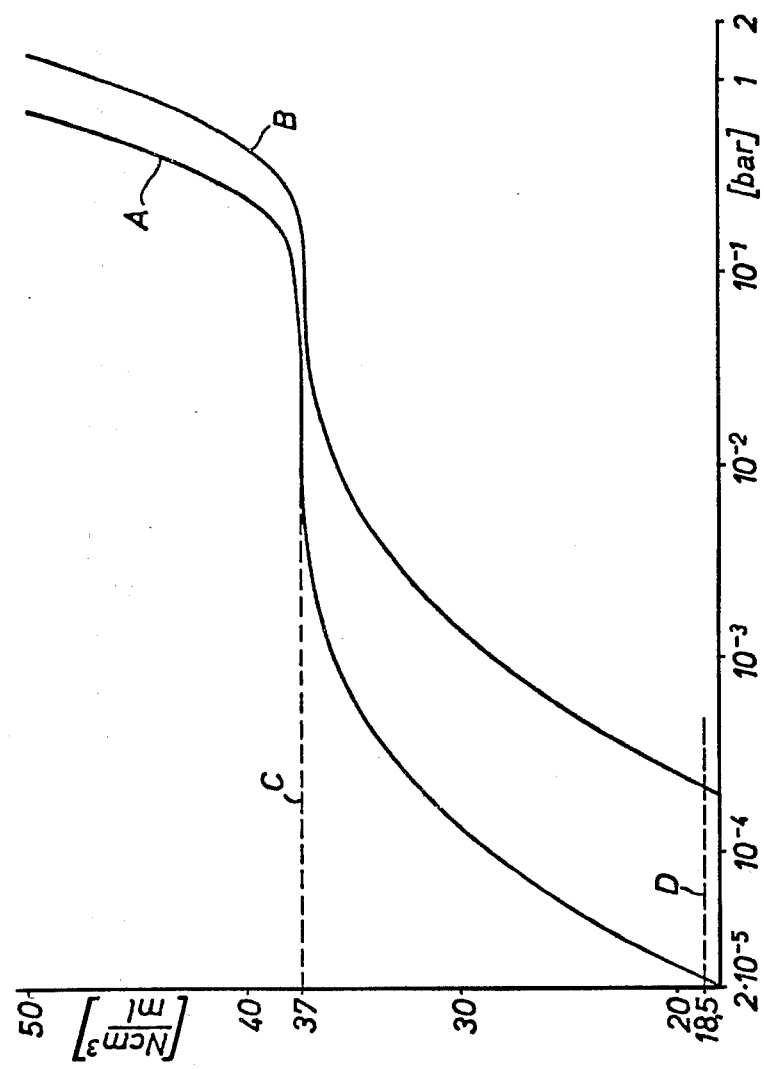
FIG. 1 is a graphic representation of the absorption capacity of carbon dioxide with methanol containing ammonia therein.

Referring to FIG. 1, the diagram contained therein shows as the ordinate the amount of carbon dioxide in $Nm^3/ml$ solution, dissolved in the methanol containing the ammonia which has 37 $Ncm^3$ ammonia per milliliter of methanol, and as the abscissa shows the existing carbon dioxide partial pressure, in bar, which are applied to it. The curves shown thereon give the equilibrium charging, measured at $-40°$ C. in curve A, and at $-20°$ C. in curve B. At the point where curves A and B cross straight lines D and C, which are parallel to the abscissa, are shown the dissolved carbon dioxide and ammonia volumes in a particular relationship. In the case of straight line D, this is in the relationship 1:2, and in the case of the straight line C, it is in the relationship 1:1. The relationship of the volume of gas is therefore identical to the molar relationship, because both are relative to the normal conditions. In connection with measurements of carbon dioxide partial pressures below atmospheric, the gaseous atmosphere was filled with nitrogen up to the total pressure of 1 bar above the solution.

When $CO_2$ is injected into methanol containing ammonia (at 37 $Ncm^3/ml$) at $-20°$ C., a precipitation of $NH_4NH_2CO_2$ occurs shortly before reaching the relationship of $NH_3:CO_2=2$, which precipitate surprisingly dissolves with further injections of $CO_2$ ($NH_3:CO_2<2$). At an ammonia-carbon dioxide relationship of 1:1, a completely clear solution exists. This result can be based upon the formation of carbamic acid ($NH_2COOH$) consisting of equal molar amounts of ammonium carbamate and carbon dioxide. In the area above the straight line C, the chemical reaction capability of the solution is saturated, due to the amount of ammonia therein. The further increase in curves A and B in this area is then based on the physical solubility of the carbon dioxide in the solution. This is surprisingly nearly as high for $CO_2$ as for pure methanol.

The solid portion in the solution decreases in the area between straight lines D and C with an increasing amount of carbon dioxide, and disappears before reaching the straight line C due to the solubility of the ammonium carbamates in the solution.

At 27 $Ncm^3NH_3/ml$ methanol and less, no formation of precipitate takes place by injection of $CO_2$ therein.

An amount of water in the methanol containing $NH_3$ can eliminate the solidification. The amount of water necessary for this to occur increases with the amount of $NH_3$ in the methanol. Thus, with 10 weight percent water in the methanol at a temperature of $-20°$ C., the solidification does not exist up to almost 36 $Ncm^3NH_3ml$ methanol. At the same time, the $CO_2$ solubility decreases in such water-containing methanol in the area above line C (physically dissolved $CO_2$) with increasing amounts of water, so that an amount of water of 20 weight percent should therefore not be exceeded.

As stated, the measurements shown in FIG. 1 include an amount of ammonia in the methanol, for example, of 37 $Ncm^3/ml$. This corresponds approximately to a portion of 3.5 weight percent. The value of 0.5 weight percent which has up to now been considered to be the highest permissible (DE-OS 27 59 123) is therefore considerably exceeded. While the value of 37 $Ncm^3/ml$ methanol mentioned here is not to be considered as the ultimate limit, the temperature level of the wash and the transfer of the solution and the reaction heat play a considerable role as far as the ultimate or highest value is concerned.

By washing the gaseous mixture with methanol containing precharged carbon dioxide and ammonia, a high degree of purity can be obtained as regards separation of carbon dioxide. Thus, one can see from curves A and B, that the carbon dioxide partial pressure over the special washing liquid, which FIG. 1 refers to, amounts only to approximately $10^{-2}$ bar at $-20°$ C., which pressure further diminishes to only $10^{-3}$ bar at $-40°$ C., if the washing liquid is preloaded e.g. with 36 $Ncm^3$ carbon dioxide per ml methanol. This corresponds to the maximum obtainable purity of the washed gas at the head of the wash column above the injection point of the precharged washing liquid.

After the washing liquid consisting of methanol containing ammonia with carbon dioxide (this precharging is represented by a point in the area between the straight lines C and D) this washing liquid can now circulate without dangerous solidification of carbamates between the wash column and regeneration columns, wherein the molar relationship of $NH_3:CO_2$ between loading and regeneration varies at a value of around 1. The lower limiting value is thus determined by the $CO_2$ partial pressure in the gas to be treated. Thus, regeneration of the washing substance does not have to be done to the same degree of thoroughness as has been required in the known method. In contrast, regeneration is now carried out only to a certain point so that a particular known concentration of carbon dioxide is maintained even in the regenerated washing liquid. Regeneration can be accomplished advantageously by utilizing the operational method of DE-PS No. 843 545, i.e., by stripping with an auxiliary gas without previous heating of the charged washing liquid, or by combinations of the warm and cold regeneration.

A particular advantage realized in the utilization of a methanol wash liquid containing over 0.5 weight percent ammonia lies in the fact that the solubility capability, in the case of lighter hydrocarbons, decreases to approximately one half in comparison to pure methanol. For example, a value of 0.65 millimoles (14.6 $Ncm^3$) of propane/gram.bar was measured for the solubility of propane as a sample hydrocarbon in methanol which contained 2.2 millimoles of $CO_2$ and 1.93 millimoles of $NH_3$ per gram, while in the pure methanol 30 $Ncm^3$ of propane/gram.bar are dissolved. Since the total amount of washing liquid can be reduced, based upon the additional chemical absorption capability of the ammonia for carbon dioxide, the losses of those hydrocarbons which are carried along decrease by more than half as an end result thereof.

Figure 2:
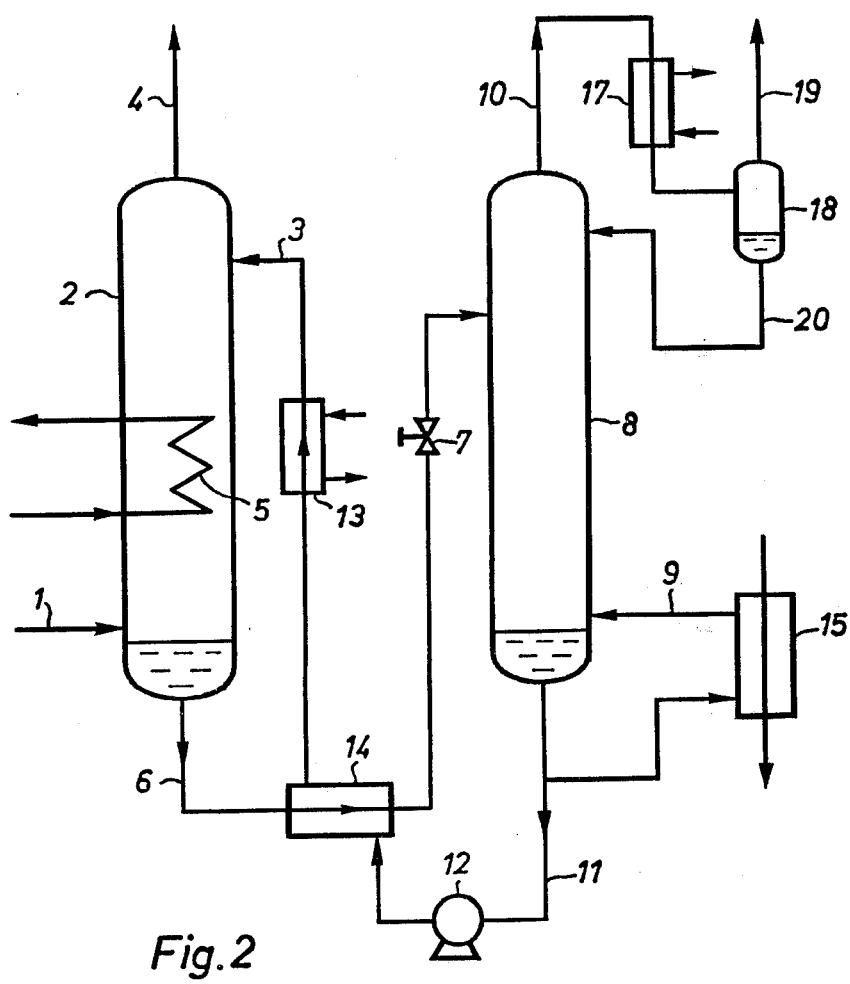
FIG. 2 is a schematic representation of the method of the present invention for washing acidic gases from natural gas.

Referring now to FIG. 2, the method of washing acidic gases, such as carbon dioxide, from natural gas is schematically shown, in a case in which the methanol washing liquid is used containing ammonia which is not completely free from $CO_2$. In that figure, through a pipe 1, 10,000 $Nm^3/h$ of natural gas, together with 3.5 volume percent $CO_2$ are cooled to $-20°$ C. and forced to a pressure of 40 bar. The natural gas rises in washing column 2 in countercurrent flow to the washing liquid which is fed into the head of the column through pipe, 3 in which it has been cleaned to a residual amount of less than 10 ppm $CO_2$. The washing liquid leaves the column through pipe 4. The washing liquid (17.5 $m^3/h$) primarily consists of methanol at the point of injection into the column 2, and contains 37 $Nm^3 NH_3$ and 27 $Nm^3 CO_2/m^3$ of washing liquid. The temperature at this point is $-40°$ C. The washing liquid drips to the bottom of the column over several exchange plates, on which a packed filling body can also be used, and during this process it enriches itself with $CO_2$ and furthermore with additional existing acid gases such as $H_2S$ which are contained in the natural gas.

The heat of absorption results in heating of the wash substance which, through indirect heat exchange, gives off the heat to the cooling substance evaporating in cooler 5. At the bottom of column 2, the loaded washing liquid collects, and at this point, it still does contain a particular portion of carried-along hydrocarbons. The temperature increase is based on the fact that the absorption heat is not completely eliminated. The amount of carbon dioxide in a washing liquid is now approximately 47 $Nm^3/m^3$ methanol.

The charged washing liquid, (i.e., containing absorbed acidic gases), reaches the regenerating column 8 through a pipe 6 from the sump through a heat exchanger 14 and a valve 7 in which a pressure of 1.15 bar and a temperature of approximately 67° C. exists. In the regenerating column 8, the laden washing liquid is separated from the $CO_2$ by countercurrent contact with the methanol vapors produced in evaporator 15, which enters through pipe 9. The $CO_2$ together with methanol vapors rise and are freed from traces of $NH_3$ in the upper portion of the column by dripping methanol condensate. The $CO_2$ methanol vapor is condensed 17, and goes into separator 18. The methanol condensate is returned to the column 8 through pipe 20 and eventually the $CO_2$, with additional acidic gases, leaves the apparatus through pipe 19.

The solvent or washing liquid freed from the previously absorbed amounts of $CO_2$ therein leaves regenerating column 8 through pipe 11 and is pumped into the heat exchanger 14 by pump 12, where it is cooled to approximately $-17°$ C. From this point, it flows through cooler 13, is cooled back to $-40°$ C., and returns to column 2. When in this same installation pure methanol is used, a circulation of 28 $m^3/h$ is necessary.

Although this invention has been described with respect to its preferred embodiments, it should be understood that many variations and modifications will now be obvious to those skilled in the art, and it is preferred, therefore, that the scope of the invention be limited, not by the specific disclosure herein, but only by the appended claims.

I claim:

1. A method for the removal of acidic gases comprising $H_2S$ or $CO_2$ from gaseous mixtures which comprises washing said gaseous mixtures with a wash stream comprising methanol containing ammonia in an amount greater than 0.5 weight percent sufficient to prevent the formation of a solid precipitate of ammonia therein, and so as to remove at least a portion of said acidic gases from said gaseous mixture and to produce a laden methanol stream containing said acidic gases therein, regenerating said laden methanol stream by removing a sufficient portion of said acidic gases therefrom, so as to regenerate said wash stream containing greater than about 0.65 weight percent $CO_2$ therefrom, and recycling said regenerated wash stream.

2. The method of claim 1 wherein said acidic gases in said laden methanol stream are chemically bonded to said ammonia therein.

3. The method of claim 1 wherein said wash stream includes water.

4. The method of claim 3 wherein said wash stream contains water in an amount of between about 1 and 20 weight percent.

5. The method of claim 1 wherein said gaseous mixture comprises a hydrocarbon-containing gaseous mixture.

6. The method of claim 5 wherein said gaseous mixture comprises natural gas.

* * * * *